United States Patent
Mesolongitis et al.

(10) Patent No.: US 8,805,088 B1
(45) Date of Patent: Aug. 12, 2014

(54) SPECULARITY DETERMINATION FROM IMAGES

(71) Applicant: Google Inc., Mountain View, CA (US)

(72) Inventors: Agis Iakovos Mesolongitis, Mountain View, CA (US); Mark Alan Duchaineau, Livermore, CA (US); Jonah Jones, San Francisco, CA (US)

(73) Assignee: Google Inc., Mountain View, CA (US)

( * ) Notice: Subject to any disclaimer, the term of this patent is extended or adjusted under 35 U.S.C. 154(b) by 0 days.

(21) Appl. No.: 14/107,210

(22) Filed: Dec. 16, 2013

(51) Int. Cl.
*G06K 9/62* (2006.01)
*G06K 9/00* (2006.01)

(52) U.S. Cl.
USPC ............ 382/216; 382/108; 382/118; 348/135

(58) Field of Classification Search
CPC ....... G06K 9/00288; G06K 9/62; G06K 9/46; G06K 9/00201; G06K 9/00248; G06K 9/00147; G06K 9/2018; G06K 9/2036; G06K 9/4661; G06K 9/621; G06F 17/30256; G06T 2207/30181; G06T 7/204; G06T 17/00; G02B 2003/0093; G01N 21/55; G01N 21/88
See application file for complete search history.

(56) References Cited

U.S. PATENT DOCUMENTS

| | | | | |
|---|---|---|---|---|
| 4,055,834 A | * | 10/1977 | Planke | 382/142 |
| 5,517,575 A | * | 5/1996 | Ladewski | 382/108 |
| 5,845,002 A | * | 12/1998 | Heck et al. | 382/110 |
| 6,064,759 A | * | 5/2000 | Buckley et al. | 382/154 |
| 6,208,997 B1 | | 3/2001 | Sigeti et al. | |
| 6,574,352 B1 | * | 6/2003 | Skolmoski | 382/103 |
| 6,694,064 B1 | * | 2/2004 | Benkelman | 382/284 |
| 7,065,242 B2 | * | 6/2006 | Petrov et al. | 382/154 |
| 7,136,171 B2 | * | 11/2006 | Tu et al. | 356/611 |
| 7,227,973 B2 | * | 6/2007 | Ishiyama | 382/103 |
| 7,253,832 B2 | * | 8/2007 | Iwaki et al. | 348/50 |
| 7,830,522 B2 | * | 11/2010 | Han et al. | 356/446 |
| 8,155,447 B2 | * | 4/2012 | Veeraraghavan et al. | 382/190 |
| 2012/0268571 A1 | * | 10/2012 | Debevec et al. | 348/48 |

OTHER PUBLICATIONS

Ahmed, "BRDF Reconstruction from Video Streams of Multi-View Recordings", Aug. 19, 2004.
Backman, "Speedup Techniques", Dept. Computing Science, Adv. Graphics, Oct. 1, 2013.
Chandraker, et al., "What an Image Reveals About Material Reflectance", 2011.

(Continued)

*Primary Examiner* — Manav Seth
(74) *Attorney, Agent, or Firm* — Lerner, David, Littenberg, Krumholz & Mentlik, LLP

(57) ABSTRACT

Aspects of the disclosure relate generally to determine specularity of an object. As an example an object or area of geometry may be selected. A set of images that include the area of geometry may be captured. This set of images may be filtered to remove images that do not show the area of geometry well, such as if the area is in a shadow or occluded by another object. A set of intensity values for the area are determined for each image. A set of angle values for each image is determined based on at least a direction of a camera that captured the particular image when the particular image was captured. The set of average intensities and the set of angle values are paired and fit to a curve. The specularity of the area may then be classified based on at least the fit.

20 Claims, 14 Drawing Sheets

(56) References Cited

OTHER PUBLICATIONS

Debevec, et al., "Estimating Surface Relectance Properties of a Complex Scene under Captured Natural Illumination", USC ICT Technical Report, Jun. 2004.

Duchaineau, et al., "ROAMing Terrain: Real-Time Optimally Adapting Meshes", Oct. 24, 1997.

Goldman, et al., "Shape and Spatially-Varying BRDF's From Photometric Stereo", 2005.

Hara, "Determining Reflectance and Light Position from a Single Image Without Distant Illumination Assumption", Proceedings of the Ninth IEEE International Conference on Computer Vision, Copyright 2003.

Ikeuchi, et al., "Determining Reflectance Properties of an Object Using Range and Brightness Images", IEEE Transactions on Patter Analysis and Machine Intellegence, vol. 13, No. 11, Nov. 1991, pp. 1139-1153.

Knecht, et al., "Interactive BRDF Estimation for Mixed-Reality Applications", Journal of WSCG, vol. 20, 2012.

Lensch, et al., "Image-Based Reconstruction of Spatial Appearance and Geometric Detail", ACM Transactions on Graphics, vol. 22, No. 3, Apr. 2003, pp. 1-27.

Li, et al., "Single-Image Reflectance Estimation for Relighting by Iterative Soft Grouping", 2002.

Lombardi, et al., "Single Image Multimaterial Estimation", Copyright 2012, pp. 238-245.

Malti, et al., "Estimating the Cook-Torrance BRDF Parameters In-Vivo from Laparoscopic Images", 2012.

Marschner, et al., "Image-Based BRDF Measurement Including Human Skin", pp. 1-15, 1999.

Murakami, et al., "Nonlinear estimation of spectral reflectance based on Gaussian mixture distribution for color image reproduction", Applied Optics, vol. 41, No. 23, Aug. 10, 2002, pp. 4840-4847.

Rusinkiewicz, "A New Change of Variables for Efficient BRDF Representation", 1998.

Sun, et al., "Time-Varying BRDFs", IEEE Transactions on Visualization and Computer Graphics, vol. 13, No. 3, May/ Jun. 2007, pp. 595-609.

Wang, et al., "Material Classification using BRDF Slices", 2009.

Yu, et al., "Inverse Global Illumination: Recovering Reflectance Models of Real Scenes from Photographs", 1999.

Zickler, et al., "Reflectance Sharing: Predicting Appearance from a Sparse Set of Images of a Known Shape", IEEE Transactions on Pattern Analysis and Machine Intelligence, vol. 28, No. 8, Aug. 2006, pp. 1-16.

\* cited by examiner

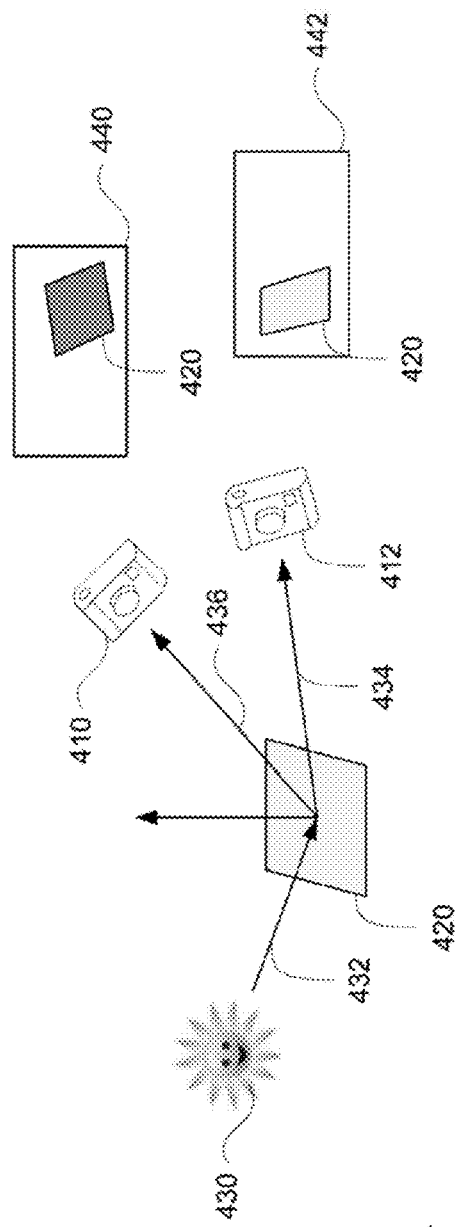
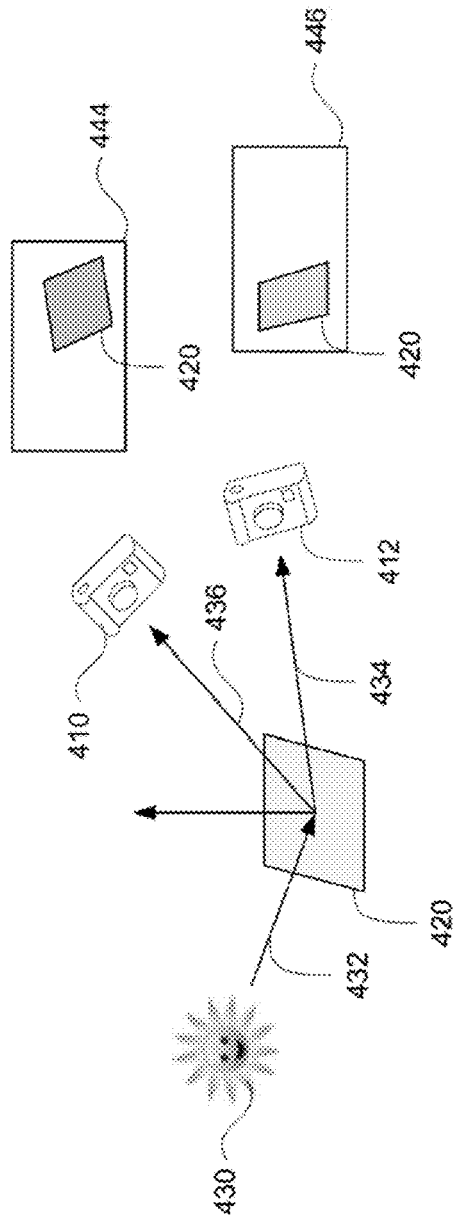
FIGURE 4A
FIGURE 4B

SPECULARITY DETERMINATION FROM IMAGES

BACKGROUND

Various systems may be used to determine specularity of an object. Typically, these systems utilize special lighting and surface conditions in laboratory settings. Thus, modeling the specularity of an object from images can become noisy and more difficult under non-laboratory settings. As an example, the number of unknowns can become very large, making processing large volumes of data for many different objects, even with a small number of images, such as 40 or less, inefficient and time consuming. In some examples, the entire process may break and provide nonsensical results.

SUMMARY

Aspects of the disclosure provide a computer-implemented method for determining specularity. The method includes selecting, by one or more computing devices, an area of geometry; identifying, by the one or more computing devices, a set of images that include the area of geometry; determining, by the one or more computing devices, a set of intensity values for the area for each image of the set of images; determining, by the one or more computing devices, a set of angle values for each image of the set of images based on at least a direction of a camera that captured the particular image when the particular image was captured; fitting, by the one or more computing devices, the set of intensity values and the set of angle values to a curve; and classifying, by the one or more computing devices, specularity of the area based on at least the fit.

In one example, determining the set of intensity values is further based on determining an average intensity value for the area in each image of the set of images. In another example, determining the set of angle values is further based on a direction of a surface normal for the area of geometry. In another example, determining the set of angle values is further based on a direction of the sun when the particular image was captured. In another example, the fit includes using an offset Gaussian curve. In another example, the method also includes using the specularity classification to provide aspects of a 3D representation of the area of geometry for display. In another example, the method also includes combining the set of average intensities and the set of angle values as a set of tuples, and wherein the fitting is further based on the tuples. In another example, the area of geometry is a 3D triangle, and wherein determining the set of intensity values of the area for each image of the set of images further includes projecting the area of geometry in 2D onto each image of the set of images. In another example the method includes receiving, from a computing device, a request for rendering an image that includes the area, the request including a camera angle, and providing, to the computing device, instructions to render the image based on the camera angle and the specularity classification of the area.

Another aspect of the disclosure provides a method for determining specularity. The method includes, dividing, by one or more computing devices, an object into a set of polygon-shaped surface geometry patches; for each particular patch of the set of polygon-shaped surface geometry patches, determining, by the one or more computing devices, a curve fit model by identifying a set of images of the object captured at different times from different orientations and by determining an average intensity value of the particular patch for each image of the set of images; determining an angle value of the particular patch for each image of the set of images; and using, by the one or more computing devices, the curve fit model for each particular patch to determine a degree of shininess for that particular patch.

In one example, the method includes propagating, by the one or more computing devices the degrees of shininess between neighboring patches in a common surface of the object. In another example, the propagating further includes performing an erosion process and subsequently using a flood filling process using the degree of shininess for at least one of the particular patches. In another example, at least one of the curve fit models is a half-angle lobe model. In another example, the intensity values are average intensity values for the particular patch. In another example, dividing the object into the set of polygon-shaped surface geometry patches includes converting a 3D scene comprised of a plurality of triangles into a set of uniformly shaped triangles. In another example, the method also includes filtering a given set of images of a given patch by identifying combinations of camera and patch positions for the given set of images, determining visibility of the given patch to the camera positions based on the combinations, and determining visibility of the given patch to the sun at the time each image was captured. In another example, each particular model curve fit is determined further based on an assumption that a maximum of angle value of the set of the angle values for that particular model curve fit will correspond to a peak of a curve. In another example, each particular degree of shininess is further determined based on a relative peak height of the model curve fit. In another example, each particular degree of shininess is further determined based on a threshold value for a height of the model curve fit.

A further aspect of the disclosure provides a system for determining specularity. The system includes one or more computing devices. The one or more computing devices are configured to: select an area of geometry; identify a set of images that include the area of geometry; determine a set of intensity values for the area for each image of the set of images; determine a set of angle values for each image of the set of images based on at least a direction of a camera that captured the particular image when the particular image was captured; fit the set of intensity values and the set of angle values to a curve; and classify specularity of the area based on at least the fit. In one example, the one or more computing devices are further configured to determine the set of intensity values by determining an average intensity value for the area in each image of the set of images.

BRIEF DESCRIPTION OF THE DRAWINGS

FIGS. 4A and 4B are diagrams of light reflecting off of an object in images in accordance with aspects of the disclosure.

DETAILED DESCRIPTION

Overview

Figure 1:
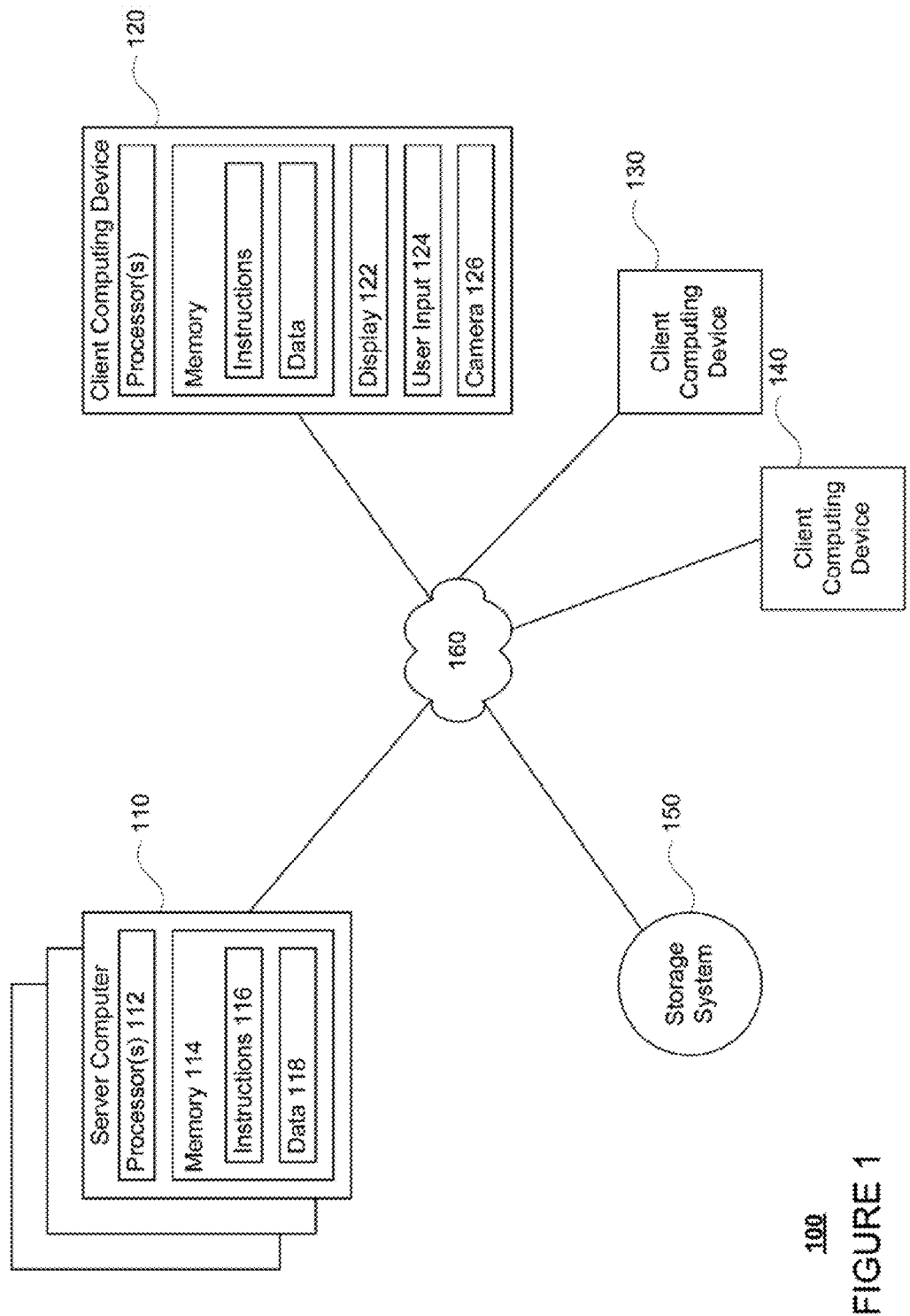
FIG. 1 is a functional diagram of an example system in accordance with aspects of the disclosure.

The technology generally pertains to determining specularity using multiple aerial photographs taken from various angles. In one example, determining whether or not a surface is of a shiny material includes determining if a surface patch is brighter when the reflected rays from the sun align with a ray coming from the camera center towards the patch. If the patch's observed intensity is high around the alignment angles and darker for further angles, then this may be an indicator for a shiny material. All other cases may be assumed to be of non-shiny materials.

By determining whether an object is shiny (or, e.g., the level of specularity of the object), such objects can be rendered in a way as to appear more realistic to a user. For example, if a user is viewing a three-dimensional (3D) model of an actual geographical location, such as a city, the specularity of objects may be used to highlight certain areas of the model such that it appears that the sun is at a specific location in the sky, etc. Thus, users may be able to see the sun reflected on buildings as the user navigates through and around the 3D model of the city. This may provide the user with the feeling that he or she is viewing a real natural environment or the actual city and not just observing a static, lifeless view.

In order to make the specularity determination, a piece of geometry may be selected. The geometry may correspond to one or more sections of a 3D mesh used to generate a 3D model of the geographic area. As an example, a "patch" may refer to a single section or a minimal surface element of the selected geometry. If the 3D mesh is comprised of triangles, a patch may thus correspond to the geographic area of a small triangle. In this regard, the specularity for a piece of geometry may be determined for each individual triangle or patch of the selected geometry. In other examples, a patch may refer to a collection triangles or a polygon of a 3D mesh.

Next, images that can possibly observe this selected geometry may be identified. For instance, the images may be part of a large group of aerial images collected by a camera mounted on an airplane or drone. In this regard, there may be several images of the same geometry captured from different angles.

Because it is important to identify images that observe the selected geometry well, areas that are occluded or shaded in the images may be ignored. In this regard, an occlusion check and a shadow check may be run on the geometry to ensure that a patch is visible to a camera location and sun location associated with a particular image. Patches may additionally be excluded from the fitting process due to high deviations in normal from neighbors, excessively large or small size, or highly elongated patch shape.

For each patch of the selected geometry, an average intensity value may be determined. In order to do so, the area of the patch may be projected onto the identified images where the patch is visible to the camera and the sun. The average intensity values for the patch may then be aggregated in a vector, such as a vector x.

A model of reflectance distribution may be generated for each patch using the images depicting that patch. The model may utilize only a small number of parameters to allow it to work in the presence of noise from, for example, aerial imagery taken over a period of hours to days apart and using a diverse set of cameras. As an example, aspects of a bidirectional reflectance distribution function (BDRF) that specifies excitant radiation given incident radiation for any possible directions may be used to generate these models. A full BDRF may quickly become very complex and may not be an efficient way to determine specularity directly from noisy aerial image data. In one example, this model may use various elements including, but not limited to, a cosine of an angle measured between a half-way vector and a normal to the patch. This half-way vector may refer to an angle half way between the direction of the sun and the direction of the camera that captured the image. The cosine values for the patch may then be aggregated in a vector, such as a vector y.

The vectors are then combined as tuples and a curve is fit to the tuples. As an example a tuple may be $(x_i, y_i)$, where $x_i$ is the $i^{th}$ element of vector x and $y_i$ is the $i^{th}$ element of vector y. A robust curve fitting technique, such as a non-linear least squares optimization, may be used to fit an offset Gaussian curve. The larger the difference between the relative peak height of the Gaussian and the offset level of the Gaussian, or the relative peak height, the more likely the patch is likely to be specular. In this regard, each patch may be classified as specular or not given a particular threshold value for the fit. In some examples, the specularity of a patch may be used to estimate the specularity of nearby patches, for example, using a flood fill algorithm. In addition, different curve shapes may be used to classify the patches as different types of materials. As noted above, these classifications may be used to render a more realistic view of 3D models of geographic areas.

Example Systems

Figure 2:
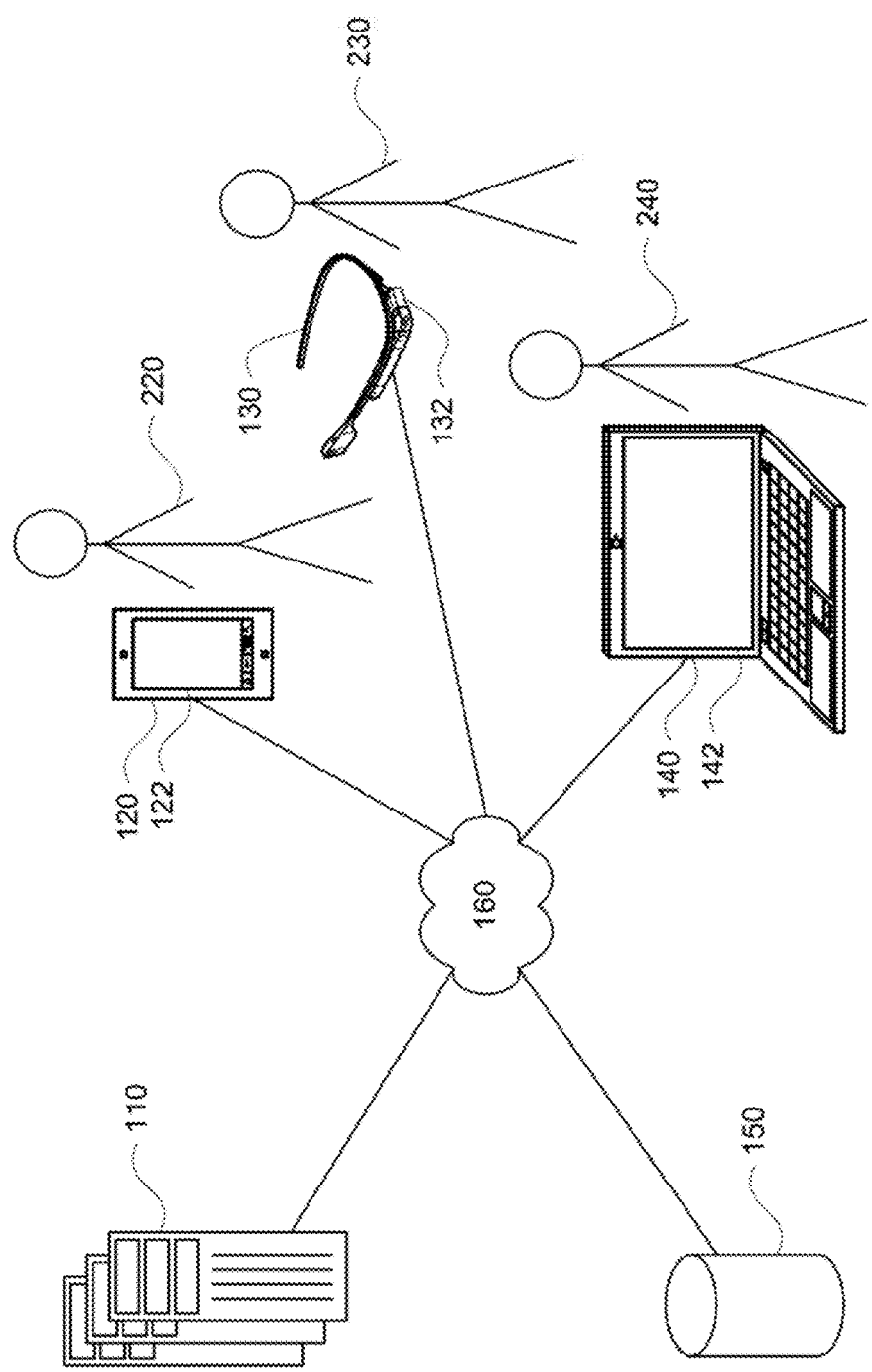
FIG. 2 is a pictorial diagram of the example system of FIG. 1.

FIGS. 1 and 2 include an example system 100 in which the features described above may be implemented. It should not be considered as limiting the scope of the disclosure or usefulness of the features described herein. In this example, system 100 can include computing devices 110, 120, 130, and 140 as well as storage system 150. Computing device 110 can contain one or more processors 112, memory 114 and other components typically present in general purpose computing devices. Memory 114 of computing device 110 can store information accessible by processor 112, including instructions 116 that can be executed by the processor 112.

Memory can also include data 118 that can be retrieved, manipulated or stored by the processor. The memory can be of any non-transitory type capable of storing information accessible by the processor, such as a hard-drive, memory card, ROM, RAM, DVD, CD-ROM, write-capable, and read-only memories.

The instructions 116 can be any set of instructions to be executed directly, such as machine code, or indirectly, such as scripts, by the processor. In that regard, the terms "instructions," "application," "steps" and "programs" can be used interchangeably herein. The instructions can be stored in object code format for direct processing by the processor, or in any other computing device language including scripts or collections of independent source code modules that are interpreted on demand or compiled in advance. Functions, methods and routines of the instructions are explained in more detail below.

Data 118 can be retrieved, stored or modified by processor 112 in accordance with the instructions 116. For instance, although the subject matter described herein is not limited by any particular data structure, the data can be stored in computer registers, in a relational database as a table having many different fields and records, or XML documents. The data can also be formatted in any computing device-readable format such as, but not limited to, binary values, ASCII or Unicode. Moreover, the data can comprise any information sufficient to identify the relevant information, such as numbers, descriptive text, proprietary codes, pointers, references to data stored in other memories such as at other network locations, or information that is used by a function to calculate the relevant data.

The one or more processors 112 can include any conventional processors, such as a commercially available CPU. Alternatively, the processor can be a dedicated component such as an ASIC or other hardware-based processor. Although not necessary, computing devices 110 may include specialized hardware components to perform specific computing processes, such as decoding video, matching video frames with images, distorting videos, encoding distorted videos, etc. faster or more efficiently.

Although FIG. 1 functionally illustrates the processor, memory, and other elements of computing device 110 as being within the same block, the processor, computer, computing device, or memory can actually comprise multiple processors, computers, computing devices, or memories that may or may not be stored within the same physical housing. For example, the memory can be a hard drive or other storage media located in a housing different from that of computing devices 110. Accordingly, references to a processor, computer, computing device, or memory will be understood to include references to a collection of processors, computers, computing devices, or memories that may or may not operate in parallel. For example, the computing devices 110 may include server computing devices operating as a load-balanced server farm. Yet further, although some functions described below are indicated as taking place on a single computing device having a single processor, various aspects of the subject matter described herein can be implemented by a plurality of computing devices, for example, communicating information over network 160.

The computing devices 110 can be at various nodes of a network 160 and capable of directly and indirectly communicating with other nodes of network 160. Although only a few computing devices are depicted in FIGS. 1-2, it should be appreciated that a typical system can include a large number of connected computing devices, with each different computing device being at a different node of the network 160. The network 160 and intervening nodes described herein can be interconnected using various protocols and systems, such that the network can be part of the Internet, World Wide Web, specific intranets, wide area networks, or local networks. The network can utilize standard communications protocols, such as Ethernet, WiFi and HTTP, protocols that are proprietary to one or more companies, and various combinations of the foregoing. Although certain advantages are obtained when information is transmitted or received as noted above, other aspects of the subject matter described herein are not limited to any particular manner of transmission of information.

As an example, computing devices 110 may include one or more web servers that are capable of communicating with storage system 150 as well as computing devices 120, 130, and 140 via the network. For example, server computing devices 110 may use network 160 to transmit and present information to a user, such as user 220, 250, or 250, on a display, such as displays 122, 132, or 142 of computing devices 120, 130, or 140. In this regard, computing devices 120, 130, and 140 may be considered client computing devices and may perform all or some of the features described below.

Each of the client computing devices may be configured similarly to the server computing devices 110, with one or more processors, memory and instructions as described above. Each client computing device 120, 130 or 140 may be a personal computing device intended for use by a user 220, 250, 250, and have all of the components normally used in connection with a personal computing device such as a central processing unit (CPU), memory (e.g., RAM and internal hard drives) storing data and instructions, a display such as displays 122, 132, or 142 (e.g., a monitor having a screen, a touch-screen, a projector, a television, or other device that is operable to display information), and user input device 125 (e.g., a mouse, keyboard, touch-screen or microphone). The client computing device may also include a camera for recording video streams, speakers, a network interface device, and all of the components used for connecting these elements to one another.

Although the client computing devices 120, 130 and 140 may each comprise a full-sized personal computing device, they may alternatively comprise mobile computing devices capable of wirelessly exchanging data with a server over a network such as the Internet. By way of example only, client computing device 120 may be a mobile phone or a device such as a wireless-enabled PDA, a tablet PC, or a netbook that is capable of obtaining information via the Internet. In another example, client computing device 130 may be a head-mounted computing system. As an example the user may input information using a small keyboard, a keypad, microphone, using visual signals with a camera, or a touch screen.

Storage system 150 may store model information as well as imagery data. The map information may include three-dimensional (3D) models of various geographic areas. As an example, the 3D models may include various features such as roads, vegetation, buildings, etc. The 3D models may be composed of a geographically located 3D mesh of triangles used to render different textures for the various features of the 3D models. As an example, the 3D mesh may be associated with geographic location information, such as latitude and longitude coordinates or other location coordinates.

The imagery data may include satellite or aerial images of various location captured from different angles at different times of day. Each of these images may be associated with geographic location information, such as latitude, longitude, altitude, and/or orientation coordinates or other location coordinates, corresponding to the location of the camera that captured the image and/or the location of one or more objects within the image. The images may also be associated with timestamp information indicating the date and time at which each image was capture as well as other information indicating camera make and model details, lens and sensor specifications, exposure time, and aperture settings.

Figure 3A:
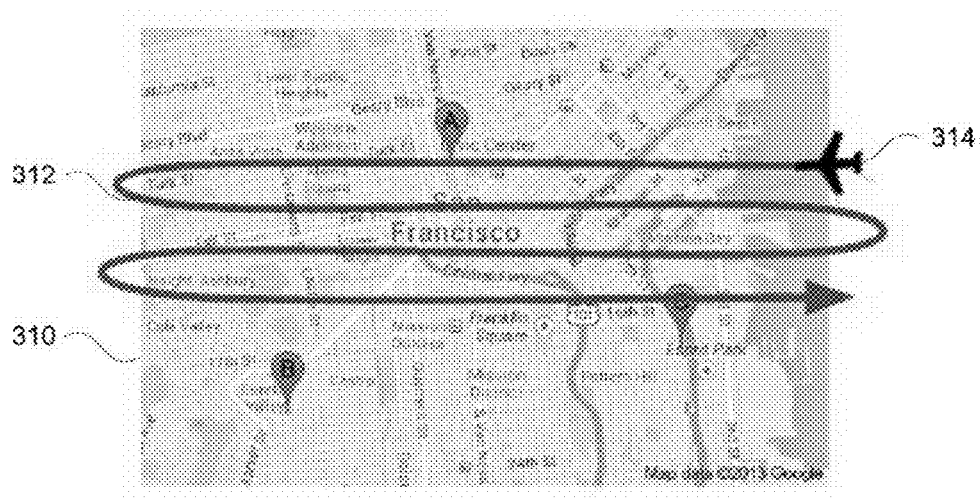
FIGS. 3A and 3B are examples of a flight path and aerial image configuration in accordance with aspects of the disclosure.
Figure 3B:
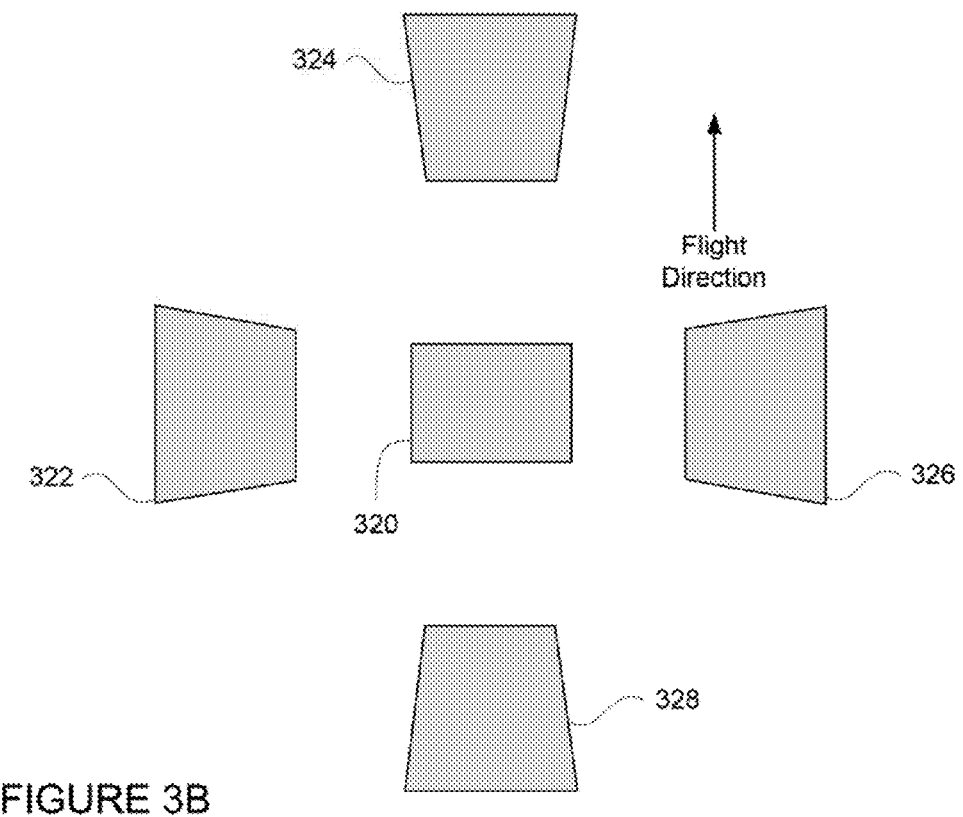

FIG. 3A includes a map 310 depicting an example flight path 312 of a plane 314, such as an airplane or drone, which may be used in order to capture such aerial images. FIG. 3B includes an example camera image configuration for plane 314. In this example, five cameras may be mounted in order to simultaneously or periodically capture a set of five aerial images 320, 322, 324, 326, and 328 of the areas below plane 314 at various angles. These images may be downloaded from the various cameras, for example using one of client devices 120, 130, or 140 and stored in storage system 150. As will be described in more detail below, these satellite or aerial images may be used to determine specularity of various objects included in the 3D model.

As with memory 114, storage system 150 can be of any type of computerized storage capable of storing information accessible by server 110, such as a hard-drive, memory card, ROM, RAM, DVD, CD-ROM, write-capable, and read-only memories. In addition, storage system 150 may include a distributed storage system where data is stored on a plurality of different storage devices which may be physically located at the same or different geographic locations. Storage system 150 may be connected to the computing devices via the network 160 as shown in FIG. 1 and/or may be directly connected to or incorporated into any of the computing devices 110-140 (not shown).

Example Methods

In order to determine the specularity of an object, a plurality of images of the object may be required. As an example, determining whether or not a surface is of a shiny material may include determining if a surface patch is brighter when the reflected rays from the sun align with a ray coming from the camera center towards the patch. If the patch's observed intensity is high around the alignment angles and darker for further angles, then this may be an indicator for a shiny material.

For example, as shown in FIGS. 4A and 4B, cameras 410 and 412 may capture images 440, 442 and 444, 446 of an object 420 from different locations and orientations at different times of day. Accordingly, the position of the sun 430 may change. Sunlight 432 may hit object 420 and reflect off of object 420 in various directions. The reflected light 434 and 436 may hit the camera lenses differently depending on the position of the sun and the camera. As is well known, the position of the sun in the sky may be determined using the timestamp of an image that provides information about the date and time an image was captured.

Depending on the specularity of object 420, object 420 may appear differently in different images depending on the reflection of light from the sun 430. As an example, if object 420 appears brighter when the reflected rays from the sun align with a ray coming from the camera 410 or 412's lense, this may indicate that object 420 is shiny or specular. All other cases may be assumed to be of non-shiny materials. Comparing FIGS. 4A and 4B, object 420 may be a shiny material in FIG. 4A, but a non-shiny material in FIG. 4B.

In order to process the images, a portion of geometry may be selected by one or more computing devices such as server computing devices 110 or client computing devices 120, 130, or 140. This portion of geometry may correspond to one or more sections of the 3D mesh used to generate one of the 3D models of storage system 150. As used herein, a patch may refer to a single section or a minimal surface element of the selected geometry. In this regard, the selected geometry may correspond to one or more patches. If the 3D mesh is comprised of triangles, a patch may thus correspond to the geographic area of a small triangle. In this regard, the specularity for a piece of geometry may be determined for each individual triangle or patch of the selected geometry. In other examples, a patch may refer to a collection triangles or a polygon of a 3D mesh. In addition, the triangles of the mesh may also be reconfigured into a set of modest-sized, generally uniformly shaped triangle patches by iterating longest-edge bisection and edge collapse operations. As an example, these patches may have a mean edge length of 2-3 meters.

Next, a set of images that could possibly observe each patch of the selected geometry may be identified. For instance, the computing device may identify the geographic location or locations of the 3D mesh corresponding to a particular selected patch or set of patches that corresponding to the selected geometry. This identified geographic location may be used to select of a set of images from the imagery data of storage system 150 based on the geographic location information associated with the imagery data. As an example, images taken from and/or of the same or a similar location may be identified. In addition, this set of images need not be significantly large. As an example, a set may include 6 or more images if the images are captured at different orientations and different times, though more images may also be used.

Figure 5A:
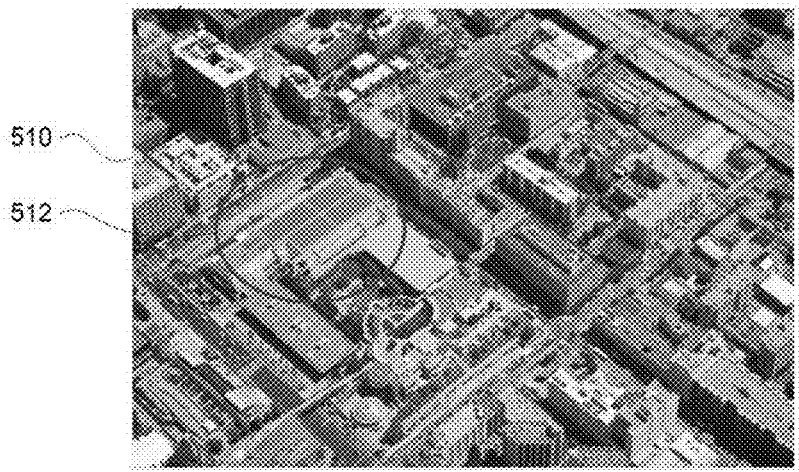
FIGS. 5A and 5B are example images of objects in accordance with aspects of the disclosure.
Figure 5B:
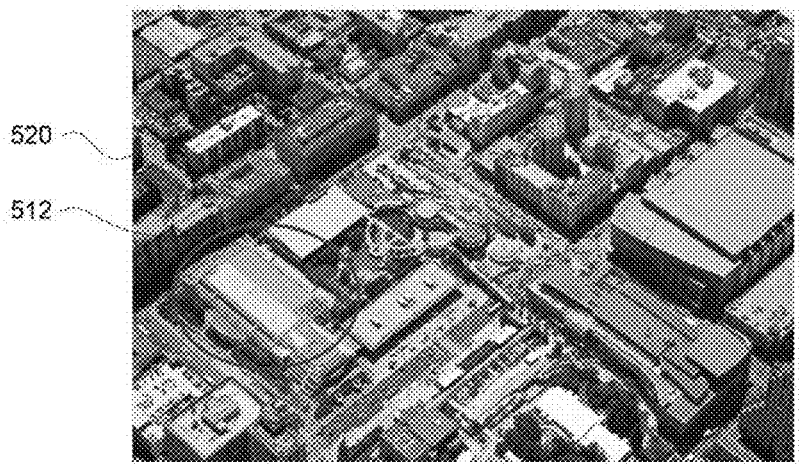

FIG. 5A is an example of an image 510 including an object 512. In this example, object 512 corresponds to solar panels on the roof of a building. Here, object 512 may correspond to an object having the same geographic location of geometry that was selected by the computing device. FIG. 5B is another example of an image 520 that also includes object 512. Together, images 510 and 520 may make up a set of images, along with one or more other images that may include object 512.

The set or sets of images may be filtered to remove images or patches where the corresponding patch for that set of images is occluded or shaded. In this regard, an occlusion check and a shadow check may be run on the geometry to ensure that a particular selected patch is visible to a camera location and sun location associated with a particular image. The occlusion check may be performed by rasterizing a two-dimensional projection of a patch onto each image on a depth-buffer. If the patch is a triangle, the projection may correspond to a two-dimensional (2D) triangle or the pixels that correspond to that triangle. The patch is then rasterized again, and the number of pixels validated by the depth-buffer is counted. If some, all, or a value between these of the pixels corresponding to the projection lie behind some nearer geometry, the projection and corresponding image, may be rejected. In other words, an image may be rejected if that patch is (mostly or partially) hidden behind some nearer geometry, such as other triangle(s) of a triangular mesh, from the point of view of the camera taking the image. If all of the images for a set are rejected, the selected patch may also be rejected. Thus, patches that are not visible by the one or more cameras that captured the images may be rejected or excluded from the specularity determination.

Similarly, for the shadow check, a projection of a patch on each image may be rasterized on an image taken from an artificial orthographic camera that emulates the sun. Then, every projection and image may also checked for validation with the sun raster image. If all of the images for a set are rejected, the selected patch may also be rejected. Thus, patches that face the sun, specifically where the sun direction is in the same side of the patch as its surface normal, i.e. has a positive dot product with the normal, may be used, while those that do not face the sun may not. Images may also be rejected if there is another patch in the depth buffer having samples that are closer to the sun. In other words, an image may be rejected if that patch is (mostly or partially) hidden behind some nearer geometry, for example other triangles of a triangular mesh, from the point of view of the sun at the time the image was taken.

Patches may additionally be rejected from the specularity determination based on their characteristics. As an example, a patch may be excluded due to high deviations in normal from neighbors, excessively large or small size, or highly elongated patch shape. In this regard, patches having geometry that is too narrow, such as a triangle that is too sharp, or patches that are tiny (e.g., <50 pixels) may be rejected.

For each patch of the selected geometry, an intensity value may be determined for each image of the set of images. Again, this set of images may be filtered as described above. In order to do so, the area of the patch may be projected onto each image of the set of images. The intensity value may correspond to the average intensity or brightness value for a patch. These intensity values of a set of images for a particular selected patch may then be aggregated in a vector, such as a vector x.

A model of reflectance distribution may be generated for each selected patch using the set of images. As noted above, the model may utilize only a small number of parameters to allow it to work in the presence of noise from, for example, aerial imagery taken over a period of hours to days apart and using a diverse set of cameras. Aspects of a BDRF that specifies exitant radiation given incident radiation for any possible directions may be used to generate these models.

In one instance, the computing device may determine an angle value based on the camera location and orientation as well as the location of the sun for each image of the set of images. This angle value may also be based on the orientation of a projection of the location of the patch on the image. As an example, an angle value may correspond to a cosine of an angle measured between a unit half-way vector and a normal to the patch. This unit half-way vector may refer to an angle half way between the direction of the sun and the direction of the camera that captured the image. In one instance, the unit half-way vector h for a given patch image may be determined from the equation:

$$h = \frac{s+c}{\text{norm}(s+c)},$$

where s refers to the direction of the sun (the direction to the sun from the location of the patch when the image was captured) and c refers to the camera direction (the direction of the camera when the image was captured). Thus, the cosine of the angle value for a single patch image may be determined from the cosine of the angle between h and n, where n is the surface normal of a particular selected patch (a vector that is perpendicular to the path and away from it, so that the angle between n and the ray from the patch to the camera is less than 90 degrees). The angle value may also be determined from the value of dot(h,n) where dot is the dot product. The angle values of a set of images for a particular selected patch may also be aggregated in a vector, such as a vector x.

Figure 6A:
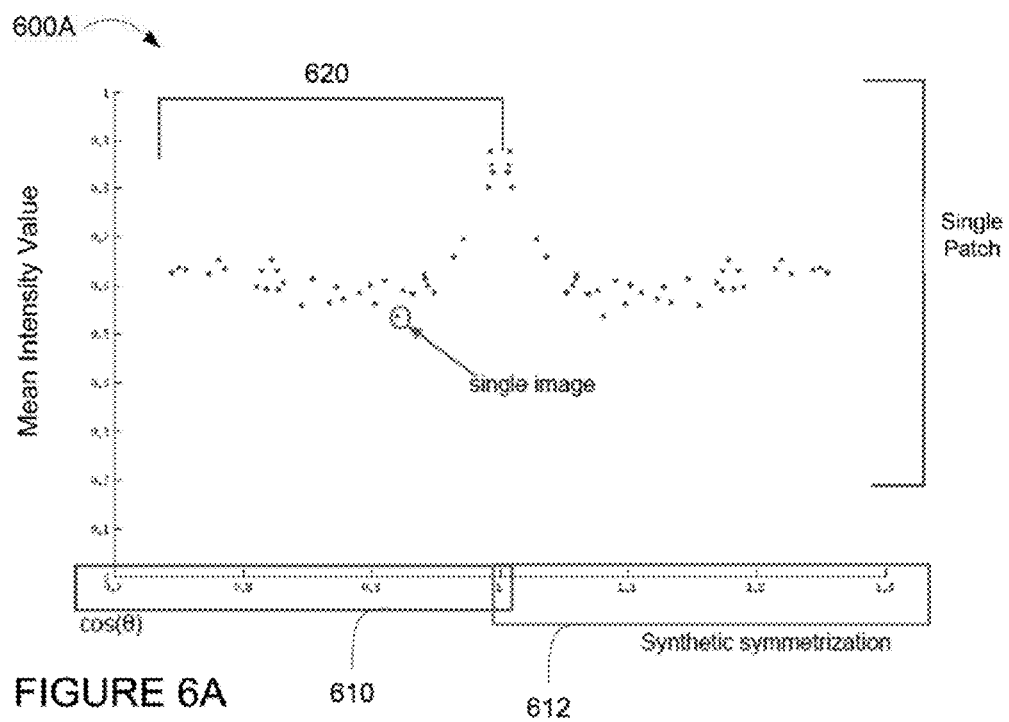
FIGS. 6A and 6B are graphs of example data in accordance with aspects of the disclosure.

FIG. 6A is an example graph 600A. Graph 600A plots cosine values by mean intensity value for a patch of object 512 depicted in images 510 and 520. The range 610 indicates actual cosine values, while the range 612 indicates a set of synthetic symmetrical data for demonstrating symmetry as discussed in more detail below. Thus, the data points below bracket 620 correspond to the tuples of the x and y vectors discussed above. In addition, each individual point also corresponds to a single image.

The intensity and angle values for each image may be combined as tuples, the resulting data points may be fit to a curve for a particular selected patch. A robust curve fitting such as a robust non-linear least squares optimization may be used to fit an offset Gaussian curve. The client computing device may do so with the assumption that the value of $x_i=1$ will correspond to the center of a Gaussian curve. As an example, a three parameter curve may be used, according to the equation:

$$y_i = \alpha + \beta e^{\left(\frac{(x_i-1)^2}{\sigma^2}\right)}.$$

Here, $x_i=\text{dot}(h,n)$, where i is a particular image of a set of images for a particular selected patch. The angle value $x_i=1$ corresponds to the alignment between the reflected rays from the sun and the viewpoint of the camera. This corresponds to the peak of the Gaussian curve if the material is specular. The value σ represents the width of the lobe of the curve. This may not always provide an accurate measure of how mirror-like is the object depending upon the sparseness of measurements. The value α represents an albedo-like average color of the object, and the value β represents the height of the lobe over or relative to any offset.

Figure 6B:
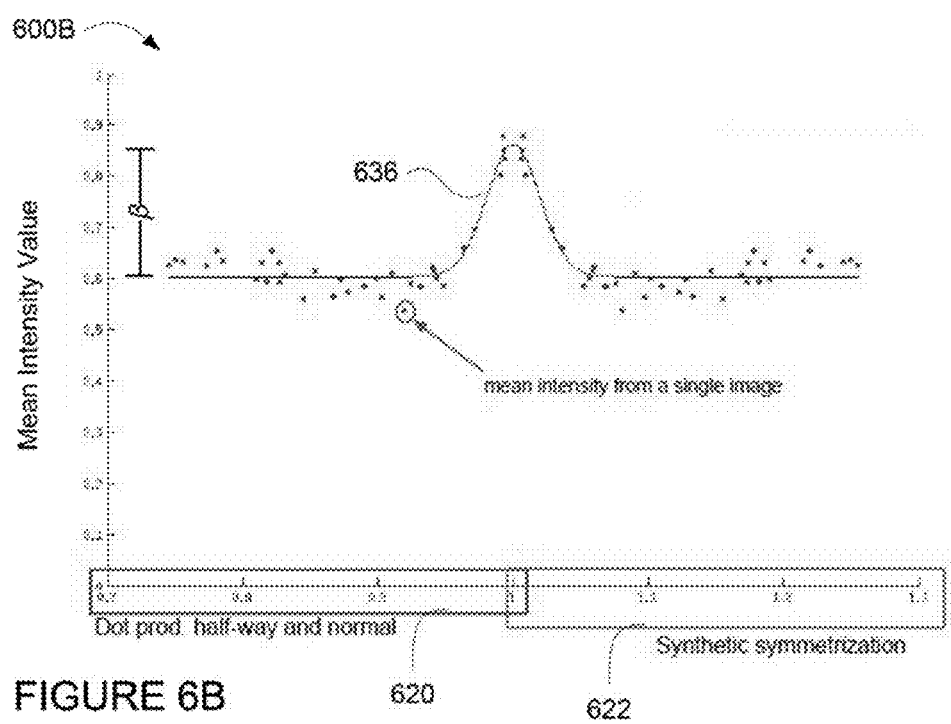

FIG. 6B is an example of a curve fitting using the data of FIG. 6A and the example equations described above. In this regard, graph 600B plots the dot product values by the mean intensity values for images of a particular selected path. Again, data points corresponding to range 620 are real while data points corresponding to range 622 are synthetic symmetrical data points. Curve fit 636 demonstrates the bell-shaped nature of real and synthetic symmetrical data points.

The larger the peak or lobe of the curve over or relative to offset, the more likely the patch is to be specular. In other words, the larger the difference between the relative peak height of the Gaussian and the offset level of the Gaussian, the more likely the patch is to be specular. This difference may be represented by the value β. Thus, the value β may be the primary indicator of shininess; the larger this value, the greater the specularity or shininess of the patch. As an example, β>0.15 may signify the existence of a specular lobe.

The relative peak height of the lobe or the value of β of curve fit 636 of FIG. 6B centered, as expected, around the value $x_i=1$ and is relatively large (e.g. on the order of 0.25). This may indicate that the corresponding patch of object 512 is shiny or specular.

Figure 7:
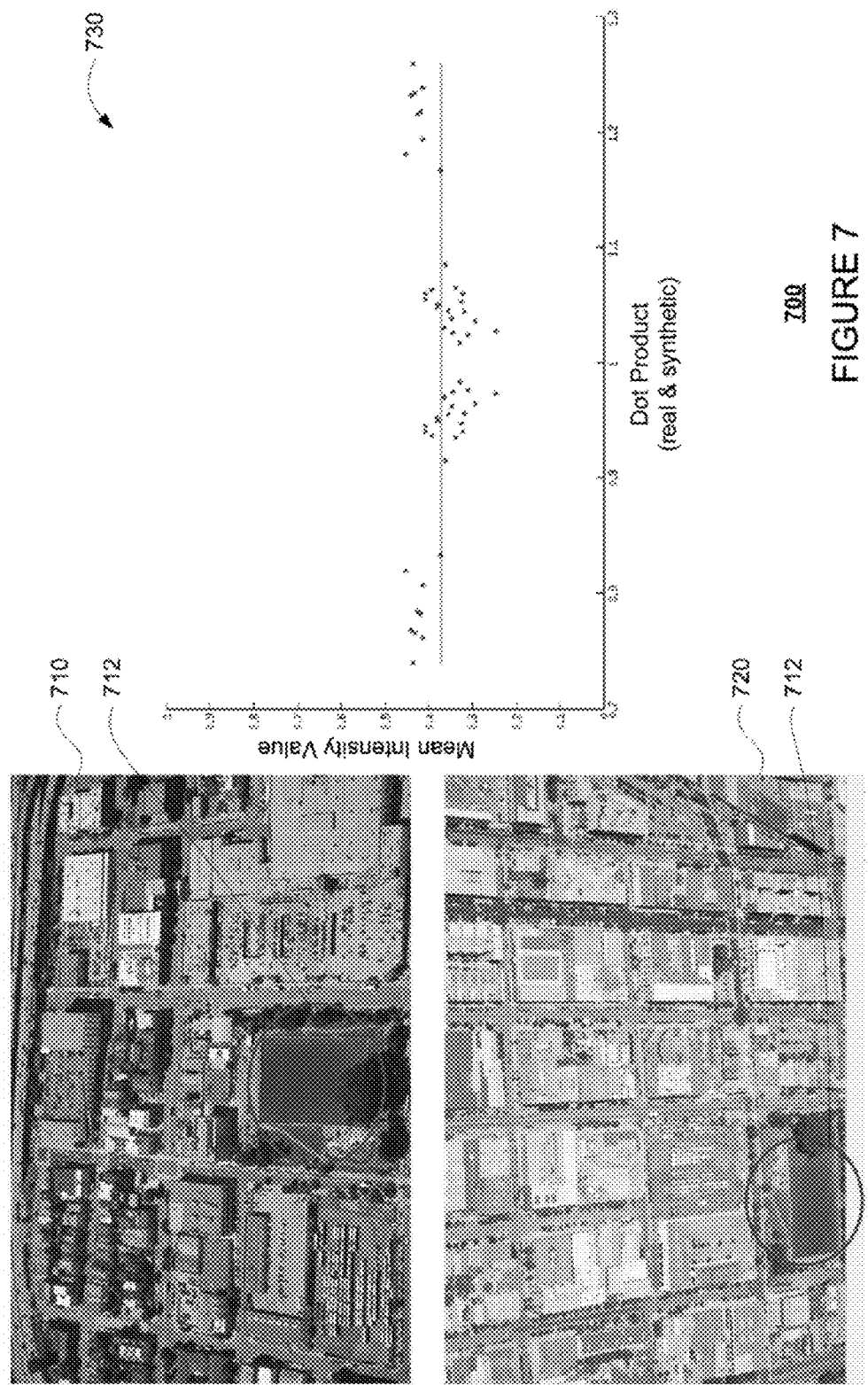
FIG. 7 is an example of images, objects, and graphs of example data in accordance with aspects of the disclosure.

FIG. 7 is an example of images 710 and 720 including a soccer field 712. FIG. 7 also includes a graph 730 of the dot products, real and synthetic, and mean intensity values of a set of images that includes images 710 and 720. In this example, the soccer field is not very specular and thus, there is no positive lobe. Accordingly, the value of β may be very small or even negative.

Figure 8:
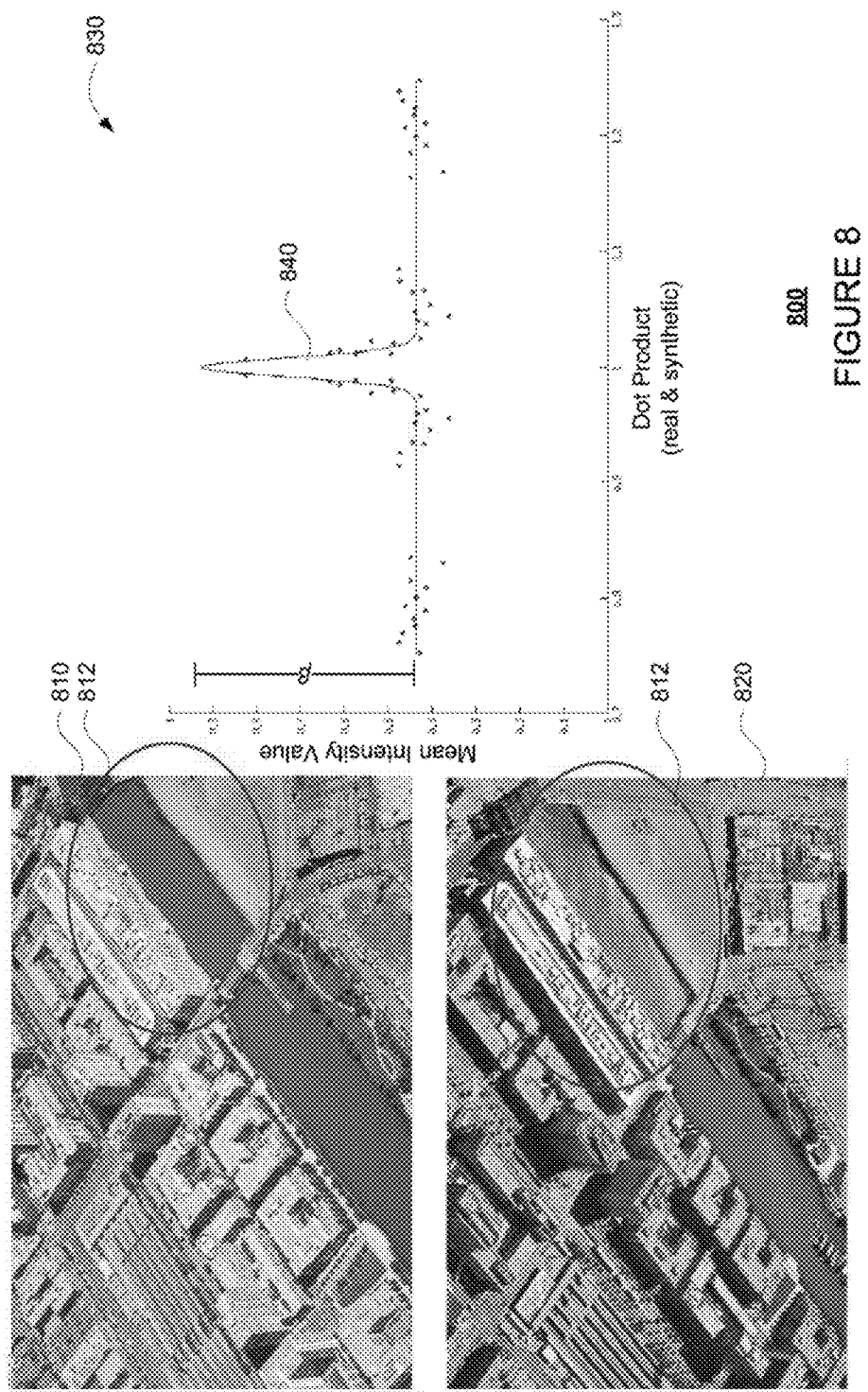
FIG. 8 is another example of images, objects, and graphs of example data in accordance with aspects of the disclosure.
Figure 9:
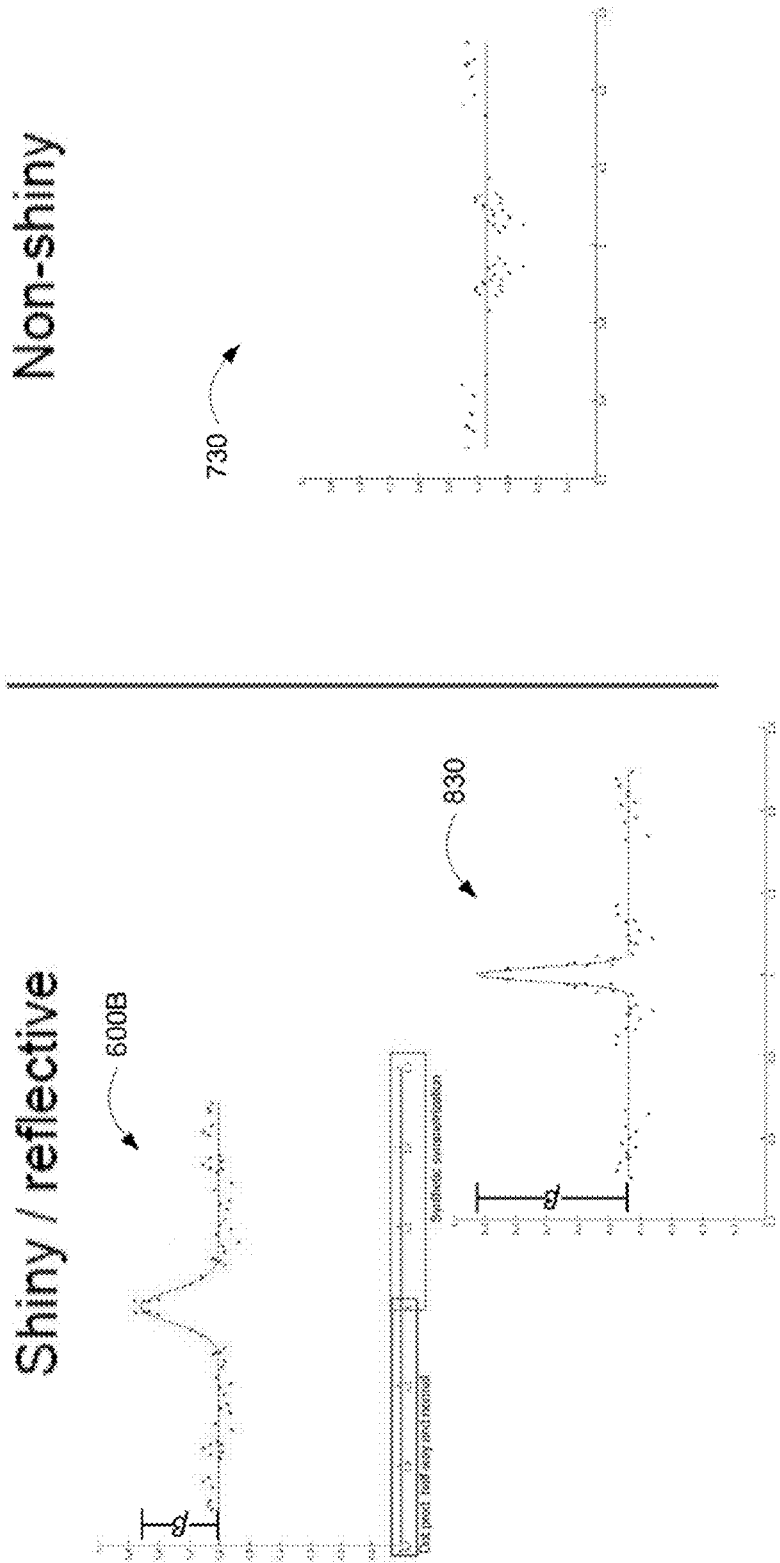
FIG. 9 is an example diagram of classifying patches in accordance with aspects of the disclosure.

FIG. 8 is an example of images 810 and 820 including a waterway 812. FIG. 8 also includes a graph 830 of the dot products, real and synthetic, and mean intensity values of a set of images that includes images 810 and 820. In this example, the waterway is very specular and thus, there is a well-defined positive lobe as can be seen from fit 840. Accordingly, the value of β may be relatively large Thus, the computing device may classify each patch based on the curve fit. As an example, using the equations above, larger values of β, such as those greater than 0.15, may indicate a specular lobe, and thus, a specular patch. In this regard, each patch may be classified as specular or not given a particular threshold value for the fit as shown in FIG. 9. For example, in FIG. 9, the respective values of are approximately 0.28 for 600B, 0.45 for 830, and 0.0 for 730. In this example, the patches of graphs 600B and 830, corresponding to the solar panels and waterway, respectively, may be classified as specular, while the patch of graph 730, corresponding to a soccer field, may be classified as non-specular.

With some patches, the data points may not be evenly distributed. In other words, there may be only a few images with very similar orientations of the camera and the sun. this may lead to false positive. Alternatively, false positives could result from the fact that data points are clustered in a flat portion of the lobe and the fit does not care about adding a Gaussian lobe or not at a region further from the measurements. In other words, there are no data points close to $x_i=1$ or within the area that would be the peak of the lobe. Consequently, such data may have a good fit either with or without a positive lobe.

In order to avoid such false positives, when a patch is classified as specular, the client device may determine whether there are any data points on the lobe and also before the lobe (in the flat region). A threshold value may be used such that the smallest measurement should be no smaller than $1$-$2\sigma$ and the largest greater than $1$-$2\sigma$. If the patch does not meet this threshold, then it may be reclassified as non-specular, unknown, or some other value.

In some examples, where there are sufficient images to get a highly confident value of $\beta$, different curve shapes may be used to classify patches as different types of materials based on $\alpha$, $\beta$ and $\gamma$ values from the offset Gaussian.

Figure 10:
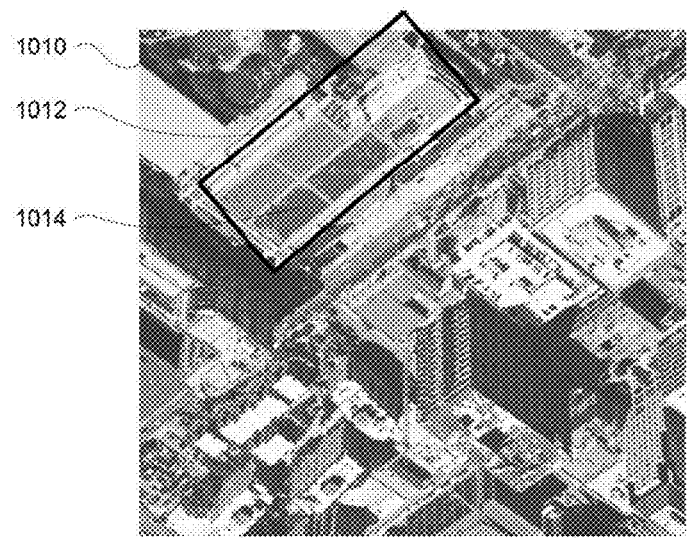
FIG. 10 is example images of 3D models in accordance with aspects of the disclosure.
Figure 10:
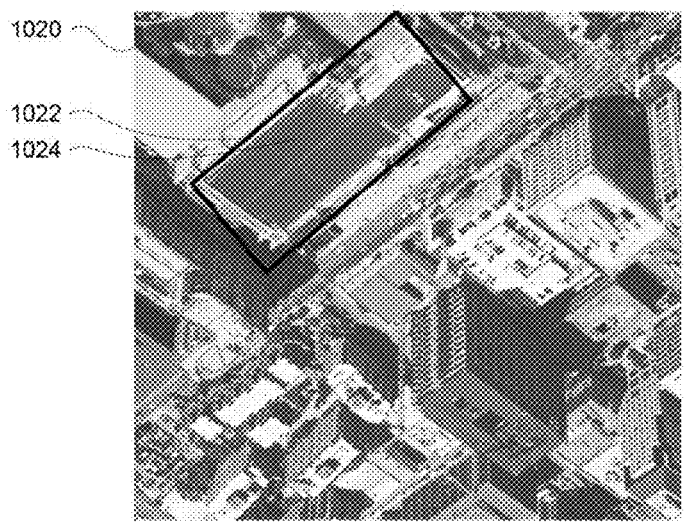

The classifying using small patches may be noisy, creating a kind of speckled output. FIG. 10 is an example image 1010 of a 3D model including a plurality of classified (or tagged) patches. In this example, the raw classifications for numerous small patches (here, triangles) are shown by the highlighted areas 1012 inside of box 1014. In this example, there are many small holes and "islands" which may correspond to false negative and false positive classifications, respectively.

This noise may be smoothed by first eliminating the small islands by shrinking the areas corresponding to specular patches using an erosion algorithm. Next, the shrunken area is expanded to cover all connected patches with a similar normal corresponding to the shrunken area using a flood fill algorithm. This may be thought of as filling out the face or roof of a building as can be seen in the examples of image 1020. In this example, highlighted areas 1022 nearly cover the roof of the building inside of box 1026. Both the erosion and the flood filling may be extended using additional information such as differences in size, shape, orientation, color and/or texture of the patches. One example would be a belief propagation algorithm that uses machine learning techniques to determine weights for differences in texture, normals, edges, etc.

As noted above, these classifications may be used to label the patches of a 3D mesh. These labels, in turn, may be used to render a more realistic view of 3D models of geographic areas. By determining whether an object is shiny (or, e.g., the level of specularity of the object), such objects can be rendered in a way as to appear more realistic to a user. One or more computing devices, such as server computing devices 110 and/or client computing devices 120, 130, or 140 may use the aforementioned labels to determine how to render a 3D model with realistic qualities.

For example, if a user is viewing a three-dimensional (3D) model of an actual geographical location, such as a city, the specularity of objects may be used to highlight certain areas of the model such that it appears that the sun is at a specific location in the sky, etc. Thus, users may be able to see the sun reflected on buildings as the user navigates through and around the 3D model of the city. This may provide the user with the feeling that he or she is viewing a real natural environment or the actual city and not just observing a static, lifeless view.

Figure 11:
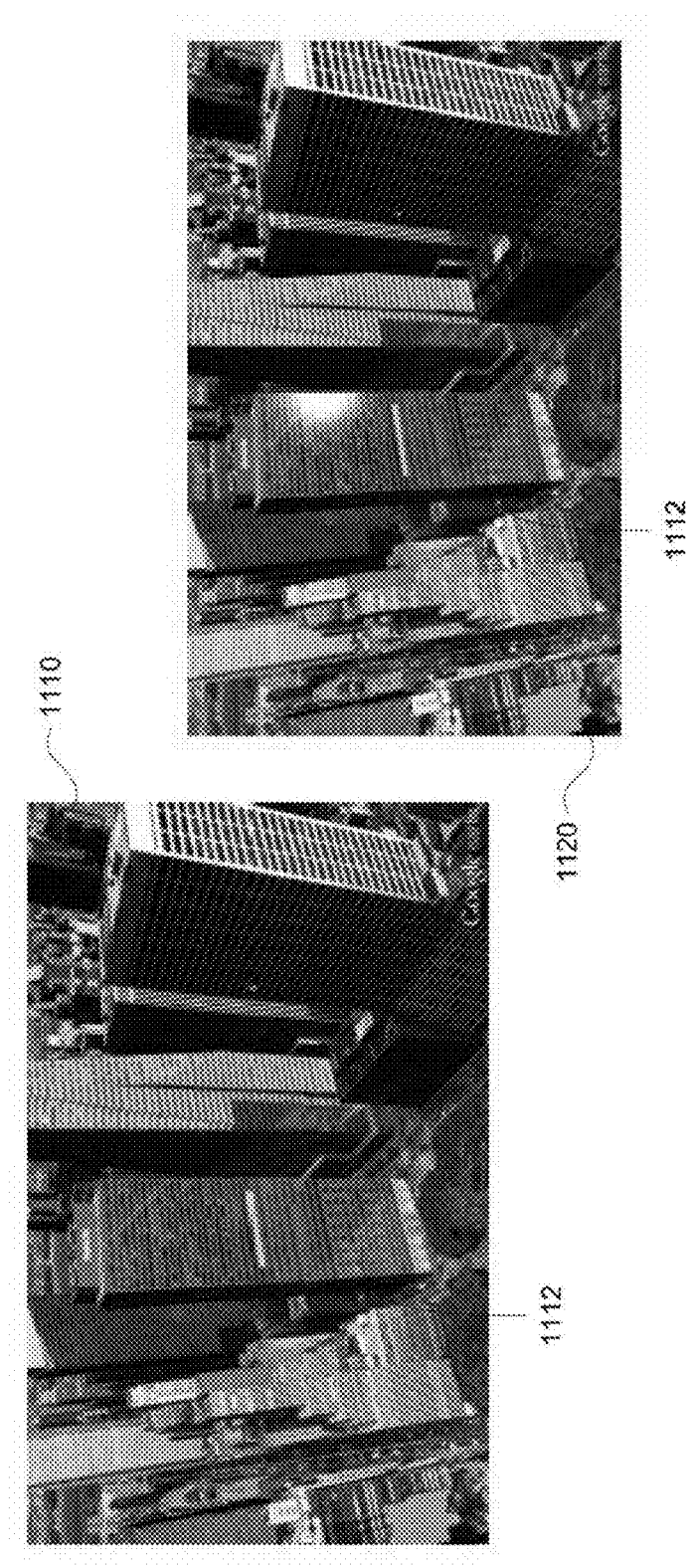
FIG. 11 is additional example images of 3D models in accordance with aspects of the disclosure.
Figure 12:
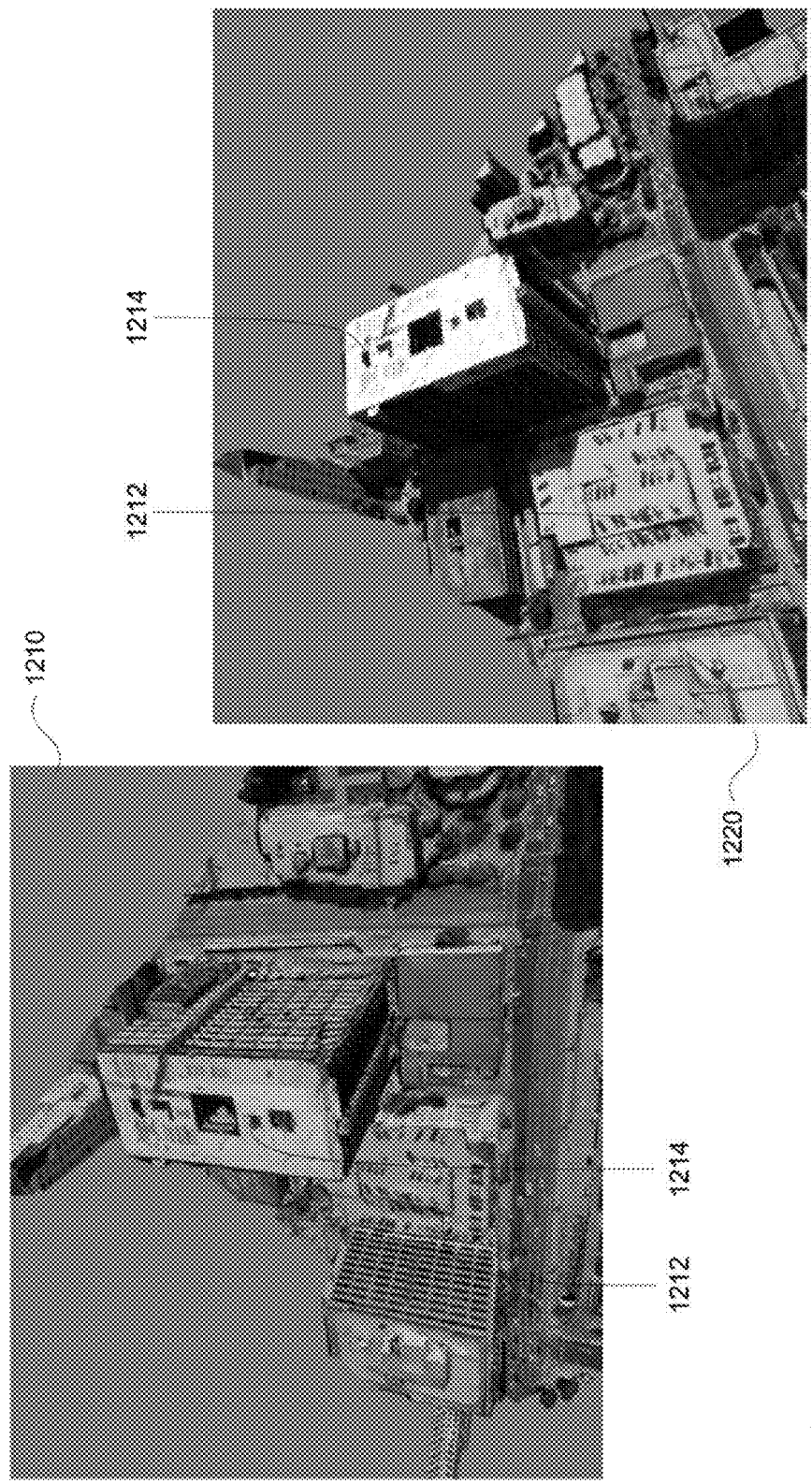
FIG. 12 is further example images of 3D models in accordance with aspects of the disclosure.

This concept is demonstrated in the examples of FIGS. 11 and 12. In the example of FIG. 11, image 1110 includes a 3D depiction of a building 1112 without differentiating between specular and non-specular patches. Image 1120 highlights some features using the specular classifications of the patches. In particular, building 1112 is shown in image 1120 as if it were reflecting the light form the sun, giving the same scene slightly more "life" in image 1120 than in image 1110. Similarly, the example of FIG. 12, image 1210 includes a 3D depiction of a parking lot 1212 and a rooftop of a building 1214 without differentiating between specular and non-specular patches. Image 1220 highlights both the parking lot 1212 and rooftop of building by showing them as if partly and fully in the path of the sun. Again, this example demonstrates how this specularity can be used to make imagery more lifelike and interesting to a viewer.

Figure 13:
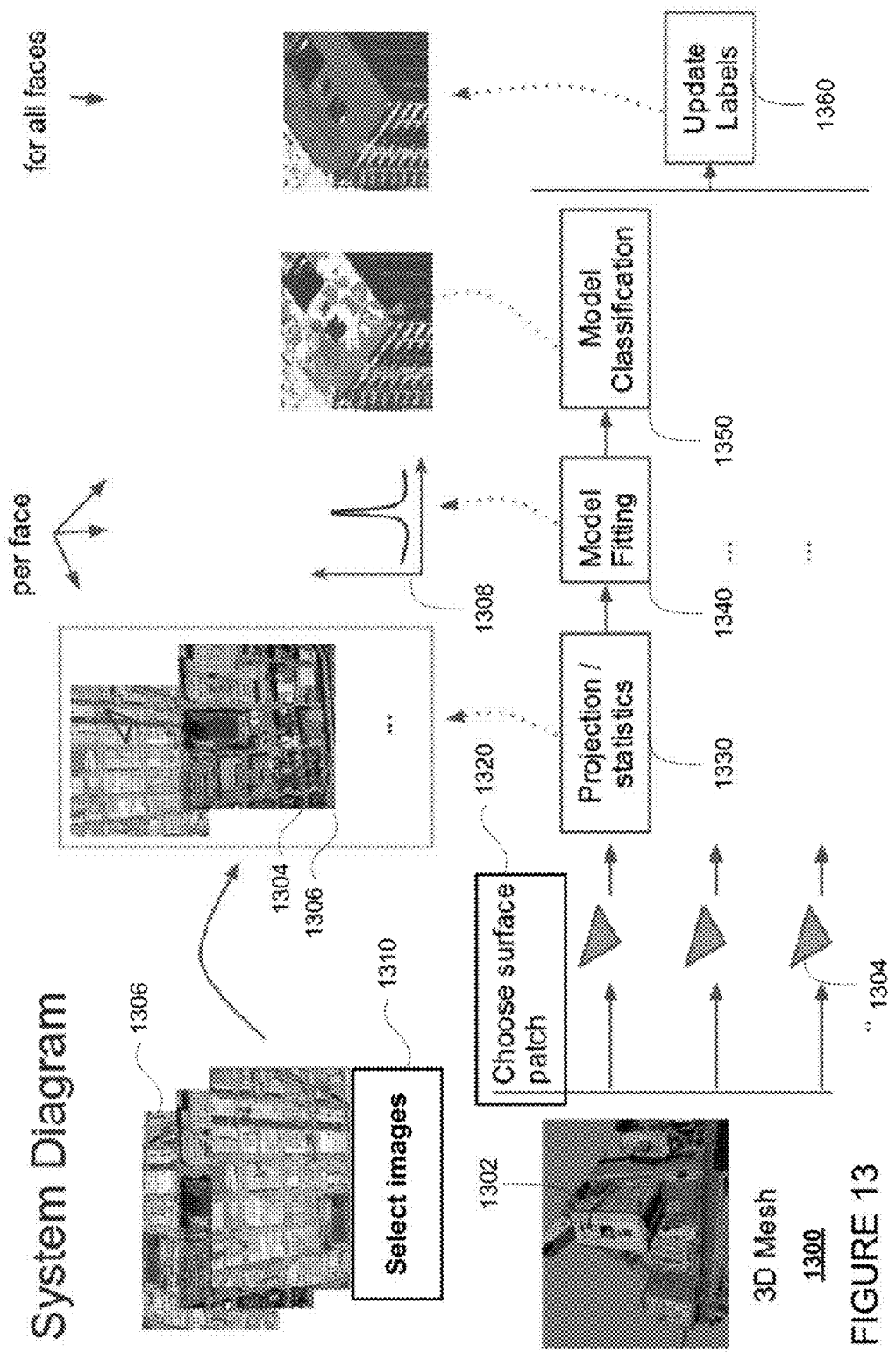
FIG. 13 is another system diagram in accordance with aspects of the disclosure.

FIG. 13 is an example 1300 of a system overview that demonstrates some of the aspects of the technology described herein. As can be seen from this example, patches 1304 of a 3D mesh 1302 are selected at block 1310. Corresponding images 1306 that include the geographic areas of those patches are selected at block 1320. The patches 1304 are projected into the images 1306 at block 1330. The various intensity and angle value statistics are determined and used to fit a model 1308 for each patch at block 1340. The fits are then used to classify the patches at block 1350. Then the patches may be labeled and used to classify and update labels nearby patches at block 1360.

Figure 14:
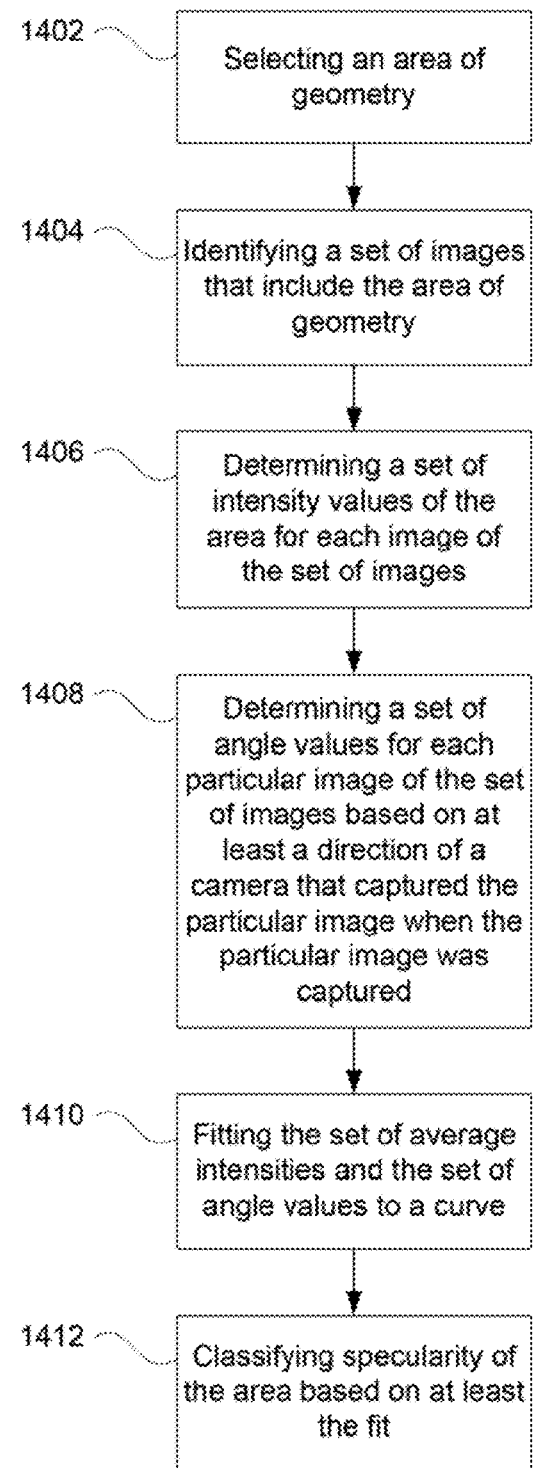
FIG. 14 is a flow diagram in accordance with aspects of the disclosure.

Flow diagram 1400 of FIG. 14 is an example of steps that may be performed by one or more computing devices, such as server computing devices 110 and/or client computing devices 120, 130, and 140, in accordance with some aspects of the technology described herein. In this example, an area of geometry is selected at block 1402. A set of images that include the area of geometry is captured at block 1404. This set of images may be filtered as described above. A set of intensity values for the area is determined for each image of the set of images at block 1406. A set of angle values for each image of the set of images is determined based on at least a direction of a camera that captured the particular image when the particular image was captured at block 1408. The set of average intensities and the set of angle values are paired and fit to a curve at block 1410. The specularity of the area is classified based on at least the fit at block 1412.

Most of the foregoing alternative examples are not mutually exclusive, but may be implemented in various combinations to achieve unique advantages. As these and other variations and combinations of the features discussed above can be utilized without departing from the subject matter defined by the claims, the foregoing description of the embodiments should be taken by way of illustration rather than by way of limitation of the subject matter defined by the claims. As an example, the preceding operations do not have to be performed in the precise order described above. Rather, various steps can be handled in a different order or simultaneously. Steps can also be omitted unless otherwise stated. In addition, the provision of the examples described herein, as well as clauses phrased as "such as," "including" and the like, should not be interpreted as limiting the subject matter of the claims to the specific examples; rather, the examples are intended to illustrate only one of many possible embodiments. Further, the same reference numbers in different drawings can identify the same or similar elements.

The invention claimed is:

1. A method for determining specularity, the method comprising:
    selecting, by one or more computing devices, an area of geometry;
    identifying, by the one or more computing devices, a set of images that include the area of geometry;
    determining, by the one or more computing devices, a set of intensity values for the area for each image of the set of images;
    determining, by the one or more computing devices, a set of angle values for each image of the set of images based on at least a direction of a camera that captured the particular image when the particular image was captured;
    fitting, by the one or more computing devices, the set of intensity values and the set of angle values to a curve; and
    classifying, by the one or more computing devices, specularity of the area based on at least the fit.

2. The method of claim 1, wherein determining the set of intensity values is further based on determining an average intensity value for the area in each image of the set of images.

3. The method of claim 1, wherein determining the set of angle values is further based on a direction of a surface normal for the area of geometry.

4. The method of claim 1, wherein determining the set of angle values is further based on a direction of the sun when the particular image was captured.

5. The method of claim 1, wherein the fit includes using an offset Gaussian curve.

6. The method of claim 1, further comprising using the specularity classification to provide aspects of a 3D representation of the area of geometry for display.

7. The method of claim 1, further comprising combining the set of average intensities and the set of angle values as a set of tuples, and wherein the fitting is further based on the tuples.

8. The method of claim 1, wherein the area of geometry is a 3D triangle, and wherein determining the set of intensity values of the area for each image of the set of images further includes projecting the area of geometry in 2D onto each image of the set of images.

9. The method of claim 1, further comprising:
    receiving, from a computing device, a request for rendering an image that includes the area, the request including a camera angle; and
    providing, to the computing device, instructions to render the image based on the camera angle and the specularity classification of the area.

10. A method for determining specularity, the method comprising:
    dividing, by one or more computing devices, an object into a set of polygon-shaped surface geometry patches;
    for each particular patch of the set of polygon-shaped surface geometry patches, determining, by the one or more computing devices, a curve fit model by:
    identifying a set of images of the object captured at different times from different orientations;
    determining an average intensity value of the particular patch for each image of the set of images; and
    determining an angle value of the particular patch for each image of the set of images; and
    using, by the one or more computing devices, the curve fit model for each particular patch to determine a degree of shininess for that particular patch.

11. The method of claim 10, further comprising propagating, by the one or more computing devices the degrees of shininess between neighboring patches in a common surface of the object.

12. The method of claim 11, wherein the propagating further includes performing an erosion process and subsequently using a flood filling process using the degree of shininess for at least one of the particular patches.

13. The method of claim 10, wherein at least one of the curve fit models is a half-angle lobe model.

14. The method of claim 10, wherein the intensity values are average intensity values for the particular patch.

15. The method of claim 10, wherein dividing the object into the set of polygon-shaped surface geometry patches includes converting a 3D scene comprised of a plurality of triangles into a set of uniformly shaped triangles.

16. The method of claim 10, further comprising filtering a given set of images of a given patch by:
    identifying combinations of camera and patch positions for the given set of images;
    determining visibility of the given patch to the camera positions based on the combinations; and
    determining visibility of the given patch to the sun at the time each image was captured.

17. The method of claim 10, wherein each particular model curve fit is determined further based on an assumption that a maximum of angle value of the set of the angle values for that particular model curve fit will correspond to a peak of a curve.

18. The method of claim 10, wherein each particular degree of shininess is further determined based on a relative peak height of the model curve fit.

19. The method of claim 10, wherein each particular degree of shininess is further determined based on a threshold value for a relative peak height of the model curve fit.

20. A system for determining specularity, the system comprising one or more computing devices configured to:
    select an area of geometry;
    identify a set of images that include the area of geometry;
    determine a set of intensity values for the area for each image of the set of images;
    determine a set of angle values for each image of the set of images based on at least a direction of a camera that captured the particular image when the particular image was captured;
    fit the set of intensity values and the set of angle values to a curve; and
    classify specularity of the area based on at least the fit.

* * * * *